(12) United States Patent
Mizokami et al.

(10) Patent No.: US 6,869,934 B2
(45) Date of Patent: Mar. 22, 2005

(54) METHOD OF PURIFYING CALCIUM ION-BINDING PROTEIN

(75) Inventors: Hiroshi Mizokami, Kumamoto (JP);
Shinichi Furukawa, Kumamoto (JP);
Keishin Sugawara, Kumamoto (JP);
Tatsufumi Onchi, Kumamoto (JP);
Kazuhiro Komatsu, Kumamoto (JP);
Satoshi Koyanagi, Kumamoto (JP);
Hideo Yoshizaki, Sayama (JP)

(73) Assignees: Juridical Foundation The Chemo-Sero-Therapeutic Research Institute, Kumamoto (JP); Kowa Company, Ltd., Nagoya (JP)

( * ) Notice: Subject to any disclaimer, the term of this patent is extended or adjusted under 35 U.S.C. 154(b) by 0 days.

(21) Appl. No.: 10/088,588

(22) PCT Filed: Jul. 18, 2001

(86) PCT No.: PCT/JP01/06209

§ 371 (c)(1),
(2), (4) Date: Mar. 21, 2002

(87) PCT Pub. No.: WO02/08249

PCT Pub. Date: Jan. 31, 2002

(65) Prior Publication Data
US 2002/0169294 A1 Nov. 14, 2002

(30) Foreign Application Priority Data
Jul. 21, 2000 (JP) ........................................ 2000-220600

(51) Int. Cl.[7] .............................................. A61K 38/00
(52) U.S. Cl. ............................. 514/20; 514/2; 514/20; 530/350; 530/417; 530/384; 530/413; 530/380; 530/425; 530/381
(58) Field of Search ....................... 514/2, 20; 530/350, 530/384, 413, 417, 380, 381, 425, 382, 405, 412, 416

(56) References Cited

U.S. PATENT DOCUMENTS 4,732,891 A 3/1988 Maki et al.
4,981,952 A 1/1991 Yan
5,258,497 A 11/1993 Reutelingsperger et al.
5,591,633 A 1/1997 Saino et al.
5,633,350 A 5/1997 Fischer et al.

FOREIGN PATENT DOCUMENTS

EP 0 731 166 A2 11/1996
JP 3-219875 9/1991

OTHER PUBLICATIONS

Bryant et al. 1983, BioChem J. vol, 211, pp. 709–716.*

Romisch, J. et al..; Biochem. J., vol. 272, pp. 223–229 (1990).

Hawthorne, T.R. et al., Journal of Biotechnology, vol. 36, pp. 129–143, (1994).

Nakao, H. et al., Chem. Pharm. Bull. 38 (7), pp. 1957–1960 (1990).

Ross, C. et al., Prep. Biochem. & Biotechnol., 28(1), pp. 49–60 (1998).

* cited by examiner

*Primary Examiner*—Bruce R. Campbell
*Assistant Examiner*—B. Dell Chism
(74) *Attorney, Agent, or Firm*—Birch, Stewart, Kolasch & Birch, LLP (57) ABSTRACT

The present invention relates to a method for purifying a calcium ion-binding protein by cation exchange chromatography. The present invention provide a method for isolating and purifying a calcium ion-binding protein in a simple and efficient manner from a liquid sample containing a calcium ion-binding protein and contaminants without any pretreatment such as addition of a chelating agent. More specifically, the present invention relates to a method for purifying a calcium ion-binding protein which comprises contacting said protein with a cation exchange carrier in the presence of calcium ions to let the said protein be adsorbed to the carrier, and after washing, eluting said protein, and to a calcium ion-binding protein having substantially no contaminants obtained by the method of the present invention.

34 Claims, 8 Drawing Sheets

Fig. 2 a)
▼ Annexin V eluted

Elution time (min.)

b)

Elution time (min.)

c)
▼

Elution time (min.)

METHOD OF PURIFYING CALCIUM ION-BINDING PROTEIN

This application is the national phase under 35 U.S.C. §371 of PCT International Application No. PCT/JP01/06209 which has an International filing date of Jul. 18, 2001, which designated the United States of America.

TECHNICAL FIELD OF THE INVENTION

The present invention relates to a method for purifying a calcium ion-binding protein by a cation exchange process. More specifically, the present invention relates to a method for purifying a calcium ion-binding protein which comprises contacting said protein with a cation exchange carrier in the presence of calcium ions to render said protein be adsorbed to the cation exchange carrier, and after washing, eluting said protein from the cation exchange carrier, and to a calcium ion-binding protein obtained by said method which contains substantially no contaminants.

BACKGROUND OF THE INVENTION

For isolation and purification of a protein of interest from contaminants, physico-chemical properties such as a molecular size, an electric charge on the surface or solubility of said protein is utilized. A process for purification commonly used in the field of protein chemistry includes, for instance, salting out, ultrafiltration, isoelectric precipitation, electrophoresis, ion exchange chromatography, gel filtration chromatography, affinity chromatography, and the like. In case that a protein of interest must be purified from the living tissues, cells, or blood, where an enormous variety of different proteins exist, these processes need often be combined in a manifold manner. However, it is possible to provide a method for purification with much more specificity by utilizing a property commonly shared by a certain kind of protein.

By way of example, a unique method for purification using anion exchange chromatography is known wherein a divalent cation-binding protein is adsorbed to an anion exchange resin and then eluted therefrom with a divalent cation to specifically purify said divalent cation-binding protein as disclosed in Japanese patent publication No. 200180/1990. According to this method, a chelating reagent such as ethylenediaminetetraacetic acid (EDTA) is added to a solution containing a divalent cation-binding protein to first remove divalent ions. Then, the resulting solution is contacted with an anion exchange resin such as MonoQ to render the divalent cation-binding protein be adsorbed to the anion exchange resin. Finally, addition of sodium chloride and calcium chloride elutes the divalent cation-binding protein from the anion exchange resin. However, most of naturally occurring proteins are negatively charged under physiological conditions and hence numerous contaminants other than a protein of interest are preferentially adsorbed to an anion exchange resin, thus hampering efficient purification of the desired protein. Therefore, this method for purification through adsorption of a desired protein to an anion exchange resin is preferably used for a small amount of a protein solution or at an advanced stage of purification processes.

Japanese patent publication No. 258286/1995 discloses a method for purifying a calcium ion-binding, vitamin K-dependent protein by an anion exchange process wherein calcium chloride is added to a solution containing a vitamin K-dependent protein and the resulting solution is passed through an anion exchange resin to isolate the desired protein from contaminating proteins. This method, however, is disadvantageous in that a large volume of fractions containing the desired protein must be passed through and hence subsequent procedures will become troublesome especially when conducted in a large scale.

Annexin V, one of calcium ion-binding proteins, is a simple protein of about 34 kDa molecular weight bearing no sugar chain that has a physiological activity such as anti-coagulating activity, corneal epithelium-extending activity, and phospholipase $A_2$ inhibitory activity. It is known that Annexin V distributes in a variety of tissues and secretions within the living body including human placenta (Chem. Pharma. Bull., 38, 1957–1960, 1990). Annexin V is called a calcium ion-binding protein since it has an ability to bind with a lipid membrane via calcium ions.

Annexin V has been extracted from organs of human or animals (Japanese patent publication No. 174023/1987). Nowadays, however, it can be produced in E. coli and yeast by the use of the genetic recombination technique (Japanese patent publications No. 20095/1989 and No. 219875/1991).

Annexin V has conventionally been purified, after pre-treatment of an Annexin V-containing solution with precipitation, membrane filtration and centrifugation, by a combination of ammonium sulfate fractionation, anion exchange chromatography, hydrophobic chromatography and affinity chromatography (Jurgen Romisch et al., Biochem. J. 272, 223–229, 1990; T. R. Hawthorne et al., Journal of Biotechnology 36, 129–143, 1994).

DISCLOSURE OF THE INVENTION

However, these processes are disadvantageous in that purification steps are complicated and troublesome requiring a great deal of labor and time and hence possibly meet an obstacle in view of reproducibility and yield, rendering them not be suitable for purification of Annexin V in an industrial scale. Moreover, as purification process in a large scale, these processes are disadvantageous in economical point of view as well since they used heparin Sepharose, which is rather expensive, for enhancing purification degree of Annexin V. Previously, the present inventors have provided a method for preparing Annexin V by pretreating a protein solution to remove contaminants to some extent and then performing anion exchange chromatography on the resulting solution (Japanese patent publication No. 219875/1991). This method might possibly enables purification of Annexin V in an industrial scale but would not exceed the method of the present invention.

As described above, for use in an industrial scale, the conventional processes are problematic in view of cost, efficiency and handling.

An object of the present invention is to provide a method for isolating and purifying a calcium ion-binding protein in a simple and efficient manner from a liquid sample containing a calcium ion-binding protein and contaminants without any pretreatment such as addition of a chelating agent.

Another object of the present invention is to provide Annexin V of high purity obtained by the method of the present invention.

Under the circumstances, the present inventors investigated for attaining the above objects and have found that Annexin V, one of calcium ion-binding proteins, is adsorbed to SP-Sepharose cation exchange carrier in the presence of calcium chloride and at pH of around neutrality. The present inventors have also noted that the adsorption of Annexin V to SP-Sepharose cation exchange carrier occurred specifically in the presence of calcium ions but could scarcely observe the adsorption in the presence of other divalent ions than calcium ions, e.g. magnesium ions. With this finding, the present inventors added calcium chloride to a large amount of homogenate of Annexin V-producing cells produced by the genetic recombination technique and contacted the resulting homogenate with SP-Sepharose cation exchange carrier which has been equilibrated with ammonium chloride buffer containing calcium chloride. After washing, elution was performed by decreasing or removing calcium chloride level or with ammonium chloride buffer containing sodium chloride in the presence of calcium ions to successfully purify Annexin V with high purity. Moreover, a trace amount of remaining proteases could successfully be removed by performing said cation exchange chromatography at pH 9.0.

Thus, the present invention encompasses a method for purification of a calcium ion-binding protein, either naturally occurring or produced by the genetic recombination technique, by cation exchange chromatography using SP-Sepharose cation exchange carrier in the presence of calcium chloride.

The present invention also encompasses a calcium ion-binding protein, either naturally occurring or produced by the genetic recombination technique, thus obtained by the method of the present invention.

BEST MODE FOR CARRYING OUT THE INVENTION

The method of the present invention comprises a step in which a liquid sample containing a calcium ion-binding protein is contacted with a cation exchange carrier in the presence of calcium ion, followed by a step in which a concentration of calcium ion is decreased or removed and/or a concentration of counter ions (salts) is increased to elute and recover said protein. The method of the present invention enables production of a calcium ion-binding protein with high purity. The contacting process with the cation exchange carrier may be performed either in a batch or by chromatography. When chromatography is used, a column size may appropriately be selected depending on a production scale.

A cation exchange carrier used herein includes, but not limited to, SP-Sepharose, CM-Sepharose, CM-cellulose, SE-cellulose, S-Spherodex, SP-Spherosil, and the like, all of which are commercially available. Among these, SP-Sepharose is preferably used.

An amount of a protein solution to be contacted with the carrier may vary depending on a concentration of the solution or an ability of the carrier for adsorption. In case of SP-Sepharose, for instance, 0.1 to 30 g/L carrier of the protein may be used. Preferably, 15 to 20 g/L carrier of the protein is used.

A flow rate while adsorption to the cation exchange carrier may be 1 to 150 cm/h, preferably 15 to 100 cm/h, more preferably 50 to 80 cm/h. On the other hand, a flow rate while elution of the adsorbed protein from the cation exchange carrier may be 1 to 150 cm/h, preferably 30 to 100 cm/h, more preferably 30 to 80 cm/h.

A buffer that may be used for adsorption to or elution from the cation exchange carrier includes any buffer conventionally used in ion exchange chromatography, including ammonium chloride buffer, citrate buffer, acetate buffer and Tris-HCl buffer. Among these, ammonium chloride buffer is preferably used. A concentration of a buffer may be in a range of 5 to 100 mM, preferably 10 to 40 mM. A buffer may be used at pH 5 to 10, preferably at pH 8 to 9.5, conditions where proteases are removed. More preferably, 20 mM (around pH 9.0) ammonium chloride buffer is used.

As a source of calcium ions, any substance that can afford calcium ions may be used, including calcium chloride, calcium carbonate, preferably calcium chloride.

When a large quantity of calcium chloride is added to homogenate of tissues or cells or plasma, hydrophobic proteins or high molecular weight compounds are sometimes deposited as a result of salting-out. Thus, calcium ions may preferably be used in such an amount that not only renders a calcium ion-binding protein be bound to and isolated from the cation exchange carrier but also forms no precipitation from a liquid sample containing a calcium ion-binding protein.

For adsorption of a calcium ion-binding protein to the cation exchange carrier, calcium ions at a concentration of 5 to 100 mM may preferably be used. More preferably, calcium ions at a concentration of 10 to 30 mM may be used. In combination with a buffer to be used for adsorption to and elution from the cation exchange carrier, 20 mM ammonium chloride buffer (pH 9.0) containing 20 mM calcium chloride may preferably be used.

The adsorbed calcium ion-binding protein may be eluted from the carrier by removing or decreasing calcium ion level in the buffer or adding other counter ions than calcium ions, or both. A counter ion includes $Na^+$, $Li^+$, $K^+$ ions, and the like. Preferably, elution may be performed by adding 1 to 500 mM, more preferably 50 to 500 mM, still more preferably 50 to 300 mM sodium chloride to the ammonium chloride buffer, and most preferably by adding 200 mM sodium chloride to 20 mM ammonium chloride buffer (pH 9.0) containing 20 mM calcium chloride. Alternatively, the adsorbed calcium ion-binding protein may be eluted from the carrier merely by decreasing the calcium chloride level to less than 5 mM.

The method of the present invention, even when used solely, can afford to provide purification of a calcium ion-binding protein of 80% purity or more. It may more efficiently be used, however, in combination with other purification processes. For example, in case that a liquid sample containing a calcium ion-binding protein is contaminated with insoluble substances, pretreatment for removing such substances, e.g. centrifugation, salting-out, membrane filtration, etc., is preferably carried out prior to the method of the present invention.

In addition to the above-described processes, other purification processes of various chromatographic procedures, including anion exchange chromatography, hydrophobic chromatography, gel filtration chromatography, affinity chromatography, adsorption chromatography, etc. may be performed together with the method of the present invention to provide a calcium ion-binding protein of higher purity. The method of the present invention may be used at any stage of the above-described processes. Preferably, after a sample containing a calcium ion-binding protein is pretreated to remove insoluble substances, the method of the present invention is used and then anion exchange chromatography is followed. More specifically, an Annexin V-containing fraction obtained by the cation exchange chromatography is applied to Q-Sepharose column equilibrated with 10 mM sodium phosphate buffer (pH 7.4) containing 50 mM sodium chloride, and after washing, elution is performed with linear gradient of concentration from 50 mM to 500 mM sodium chloride to give Annexin V with much higher purification.

A calcium ion-binding protein to be purified by the method of the present invention typically includes Annexins I, II, III, IV, V, VI and VII but may be any protein that has an ability to bind to calcium ions, such as coagulation factor X.

The method of the present invention may efficiently be applied to blood, body fluid and tissue homogenate from an animal either naturally occurring or genetically engineered that produces a calcium ion-binding protein, as well as cell homogenate and culture supernatant of recombinant cells, including plant cells, bacterial cells, yeast cells, insect cells and animal cells. preferably, the method of the present invention may be used in recombinant yeast cells producing a calcium ion-binding protein. More preferably, the method of the present invention may be used in cell homogenate or culture supernatant of yeast cells producing Annexin V.

Annexin V thus prepared, having special physiological activities, may be formulated into a pharmaceutical preparation in any conventional dosage form such as injections, eye drops, oral preparations, suppositories, etc. alone or in combination with a pharmaceutically acceptable carrier, diluent, stabling agent or preservative.

According to the present invention, an efficient method for purifying a calcium ion-binding protein with high purity is provided. Also provided is the calcium ion-binding protein thus obtained by the method of the present invention having substantially no contaminants.

According to the method of the present invention, most proteins negatively charged under physiological conditions are passed through the cation exchange carrier whereas a calcium ion-binding protein, which can form a complex with calcium ions, is preferentially adsorbed to the carrier. Thus, the method of the present invention enables handling of a large quantity of a sample at one time without deterioration of the adsorption capacity of the cation exchange carrier by contaminating proteins other than the desired protein.

EXAMPLE

Preparation Example

Preparation of Recombinant Yeast Cell Producing Annexin V

Figure 1A:
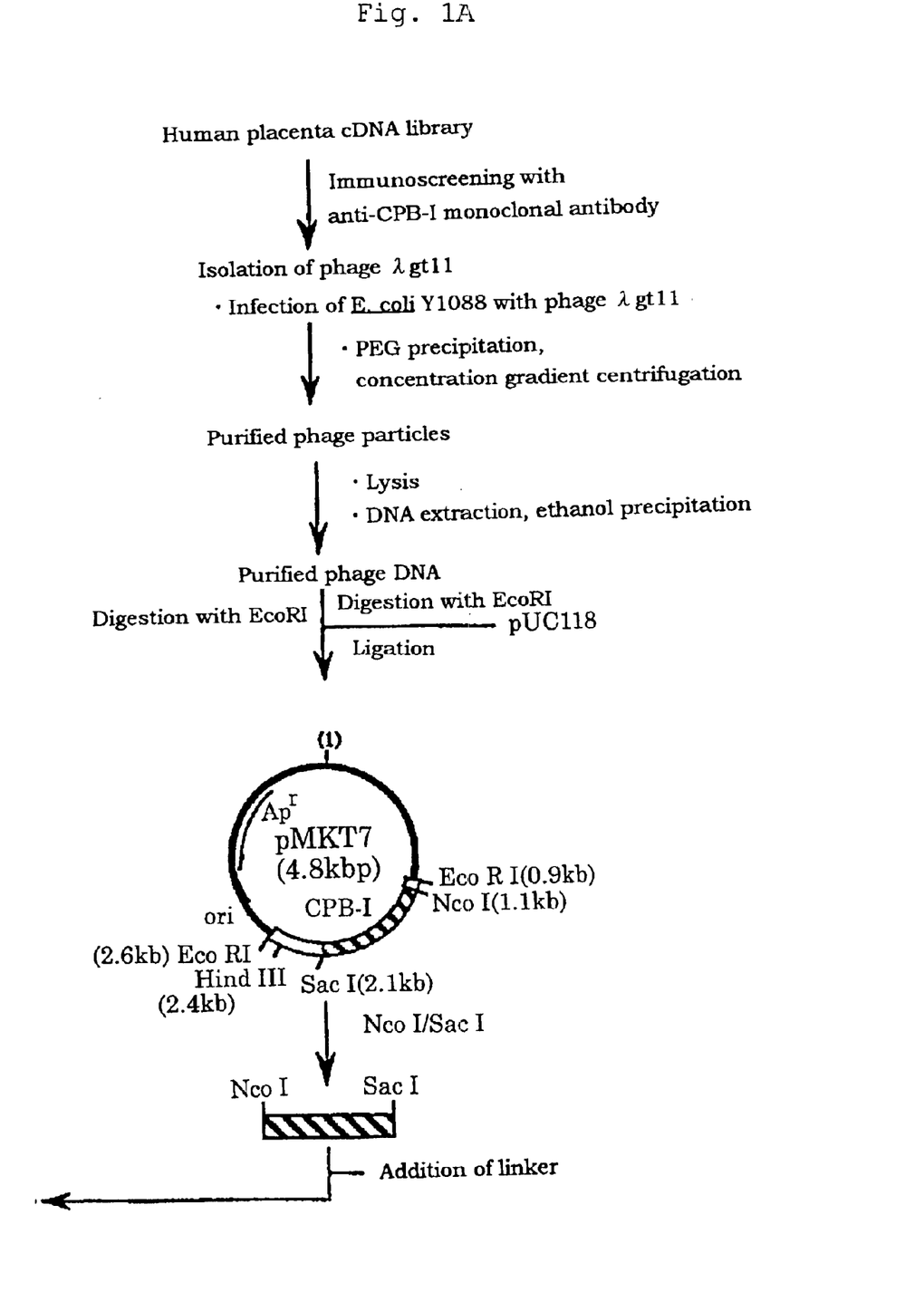
FIGS. 1A and 1B are a schematic illustration of cloning of Annexin V structural gene and preparation of yeast cells transformed with said gene.
Figure 1B:
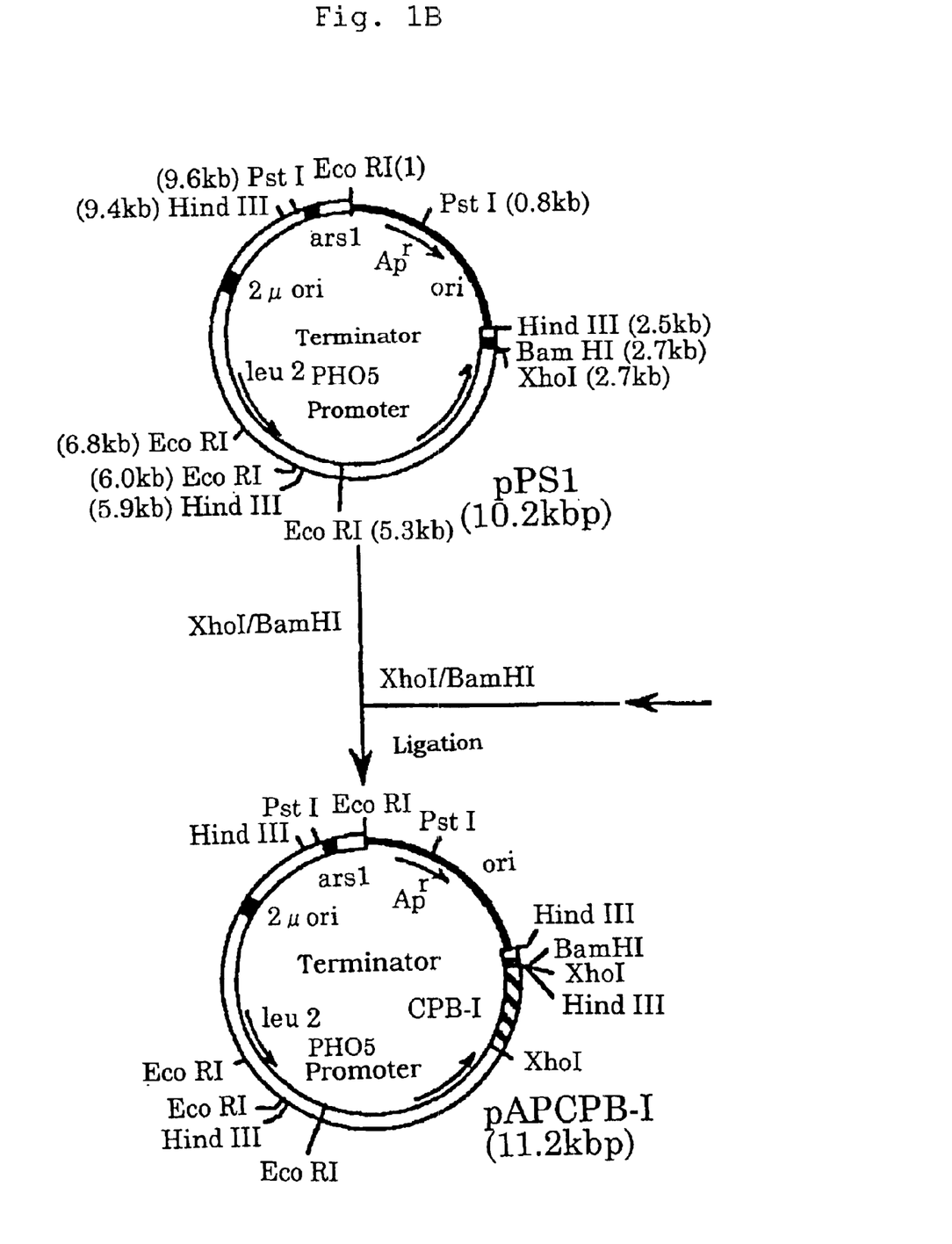

Recombinant yeast cells producing Annexin V were prepared as described in a publication of patent application (Japanese Patent Publication No. 219875/1991). FIG. 1 schematically shows preparation of the recombinant yeast cells wherein the term "CPB-I" is used for referring to "Annexin V".

(1) Cloning of Annexin V Structural Gene

From human placenta cDNA library (Clontech Laboratories, Inc.), phage that bears Annexin V structural gene was insolated by immunoscreening using anti-Annexin V monoclonal antibody. DNA was then prepared from phage and digested with restriction enzyme EcoRI to produce a fragment, which was then inserted into the EcoRI site of pUC118 vector to construct pMKT7.

(2) Construction of Expression Plasmid

The plasmid pMKT7 was digested with restriction enzymes NcoI and SacI and a DNA fragment containing Annexin V structural gene was separated by agarose electrophoresis. Addition of a synthetic linker converted both ends of the DNA fragment into XhoI and BamHI sites. The resulting DNA fragment was inserted into XhoI and BamHI sites of the expression vector pPS1 to construct expression vector pAPCPBI.

(3) Preparation of Recombinant Yeast Cells

Host yeast cells (*Saccharomyces cerevisiae* AH22) were transformed with the expression plasmid pAPCPBI by the lithium acetate technique. After transformation, colonies appeared on an agar medium deprived of leucine were isolated and an expression level was measured. Those clones with higher expression level were selected and subjected to repetition of plating to the agar medium, isolation of colonies and measurement of expression level to give recombinant yeast cells with stability.

Example 1

Purification of Recombinant Annexin V (1) Culture of Annexin V-Producing Recombinant Yeast Cells Annexin V-producing recombinant yeast cells were cultured on 2L synthetic selection medium at 28° C. for 3 days. The recombinant yeast cells were then inoculated to 88L selection medium and cultured at 28° C. for 2 days. The recombinant yeast cells were then transferred to 810L semi-synthetic medium (40 g sucrose, 5 g yeast extract, 5 g ammonium sulfate and 0.5 g magnesium sulfate septahydrate in 1L medium) and culture was continued at 28° C. for 24 hours.

(2) Pretreatment of Annexin V in Large Quantity Prior to Purification

The large culture solution was filtered with a 0.1 $\mu$m membrane filter to collect the recombinant yeast cells, which were physically ruptured with a French press-type cell homogenater. The ruptured cell suspension was filtered with the membrane filter and the filtrate was concentrated with a ultrafiltrater. To the concentrate was added acetic acid for isoelectric precipitation (pH 5.0). Precipitates formed were filtered with the membrane filter to remove the precipitates. Then, pH of the filtrate was adjusted to 9.0 with ammonia and the filtrate was again concentrated with a ultrafiltrater (pretreated solution).

(3) Cation Exchange Chromatography (Elution by Decreasing or Removing Calcium Chloride Level)

To the pretreated solution was added a calcium chloride solution to a final concentration of 20 mM and was subjected to cation exchange chromatography with SP-Sepharose (Pharmacia). Specifically, the pretreated solution supplemented with calcium chloride was applied to a column equilibrated with 20 mM ammonium chloride buffer (pH 9.0) containing 20 mM calcium chloride and 50 mM sodium chloride. After washing with the buffer, the column was further washed with 20 mM ammonium chloride buffer (pH 9.0) containing 20 mM calcium chloride. Then, Annexin V was eluted with 20 mM ammonium chloride buffer (pH 9.0).
(4) Cation Exchange Chromatography (Elution by Increasing Sodium Chloride Level)

As in the step (3), the pretreated solution was added with a calcium chloride solution to a final concentration of 20 mM and was subjected to cation exchange chromatography with SP-Sepharose. Specifically, the pretreated solution supplemented with calcium chloride was applied to a column equilibrated with 20 mM ammonium chloride buffer (pH 9.0) containing 20 mM calcium chloride and 50 mM sodium chloride. After washing with the buffer, Annexin V was eluted by a linear gradient of concentration of sodium chloride from 50 mM up to 300 mM with 20 mM ammonium chloride buffer (pH 9.0) containing 20 mM calcium chloride (flow rate at adsorption and elution: 56.7 cm/h).

Figure 2:
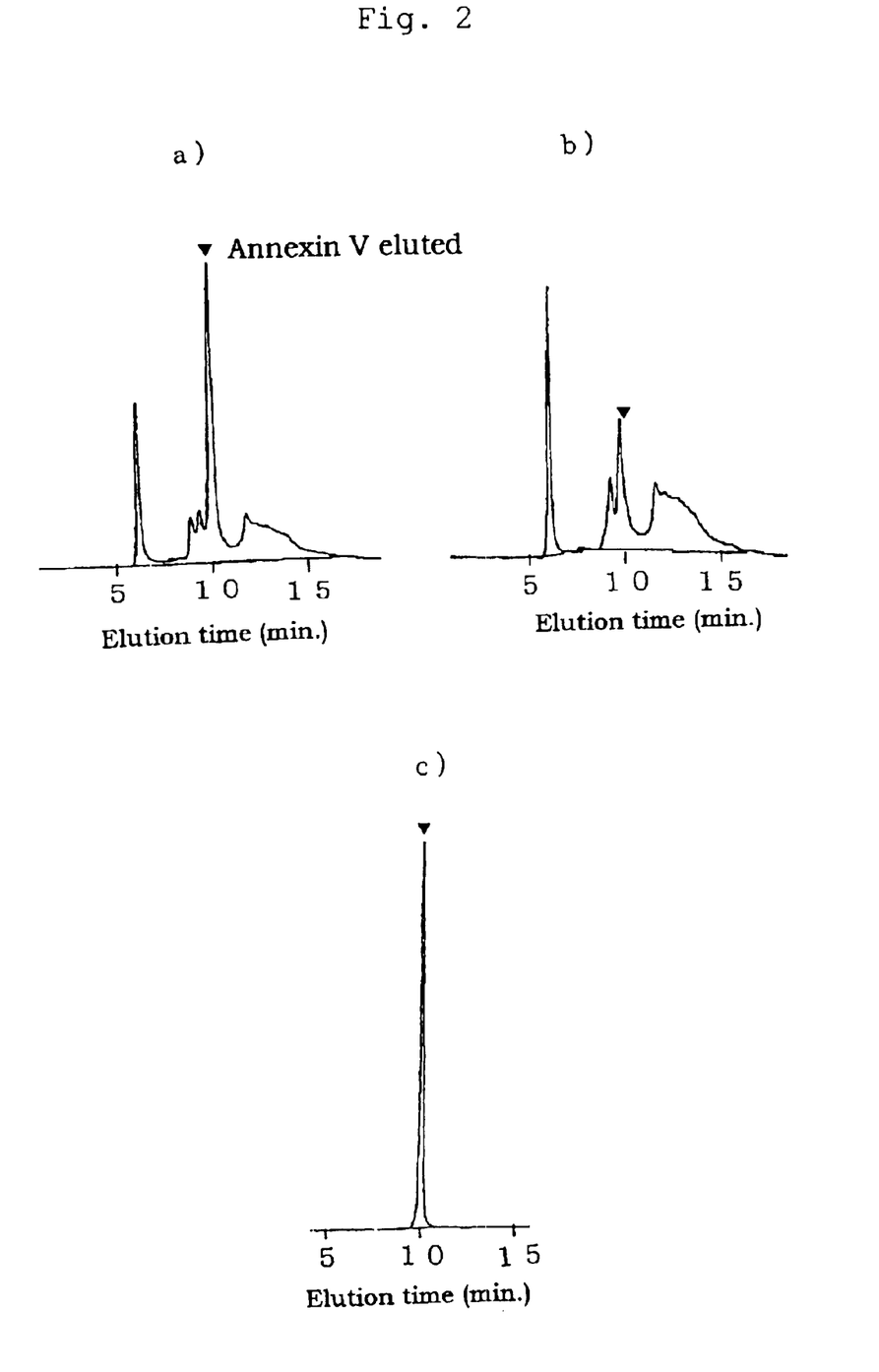
FIG. 2 shows results of gel filtration chromatography for (a) samples prior to cation exchange chromatography, (b) fractions passed through cation exchange chromatography, and (c) fractions eluted from cation exchange chromatography after washing.

FIG. 2 shows elution patterns obtained by gel filtration chromatography of (a) sample prior to cation exchange chromatography, (b) fractions passed through cation exchange chromatography, and (c) fractions eluted from cation exchange chromatography, respectively. Gel filtration chromatography was performed wherein 20 µL sample was applied to TSKgel G3000 SW×l (7.8 mm (ID)×30 cm) equilibrated with 10 mM phosphate buffer (pH 7.2) containing 0.14 M NaCl at a flow rate of 125.6 cm/h. The results of gel filtration chromatography for fractions eluted from cation exchange chromatography are shown in Table 1 wherein purity was obtained from the elution pattern.
(5) Anion Exchange Chromatography (Comparison with Conventional Technique)

Anion exchange chromatography was performed for the pretreated solution. The pretreated solution was applied to Q-Sepharose (Pharmacia) column equilibrated with 10 mM sodium phosphate buffer (pH 7.4) containing 50 mM sodium chloride. After washing, Annexin V was eluted by a linear gradient of concentration of sodium chloride from 50 mM up to 300 mM. The results of gel filtration chromatography for the eluted fractions are shown in Table 1.

Annexin V obtained by the conventional technique and that obtained by the method of the present invention were measured for their anti-coagulating activity after further purification with additional purification processes. Measurement of anti-coagulating activity was made in the same manner as the quantification of sodium heparin described in the Japanese Pharmacopoeia (the 13th revision, p.900–901). Anti-coagulating activity was calculated wherein prolongation in time for coagulation induced by 1 mg of standard sample (Annexin V purified by the conventional technique) was defined as one unit (U). As a result, no inactivation of Annexin V obtained by the method of the present invention was observed (Table 1).

TABLE 1

|  | Anion exchange chromatography | Cation exchange chromatography |
| --- | --- | --- |
| Purity (%) | 81.86 | 100 |
| Activity (U/mg) | 0.9 to 1.0 | 0.9 to 1.0 |

Example 2

Purification of Recombinant Annexin V

A recombinant Annexin V was purified as in Example 1 except that 20 mM citrate buffer (pH 6.0) containing 20 mM calcium chloride and 50 mM sodium chloride was used in place of 20 mM ammonium chloride buffer (pH 9.0) containing 20 mM calcium chloride and 50 mM sodium chloride, and 20 mM citrate buffer (pH 6.0) was used in place of a linear gradient concentration of sodium chloride from 50 mM up to 300 mM with 20 mM ammonium chloride buffer (pH 9.0) containing 20 mM calcium chloride, in the cation exchange chromatography of the step (4). Flow rate was also altered to 15.6 to 54.6 cm/h at adsorption and 39 cm/h at elution.

Figure 3:
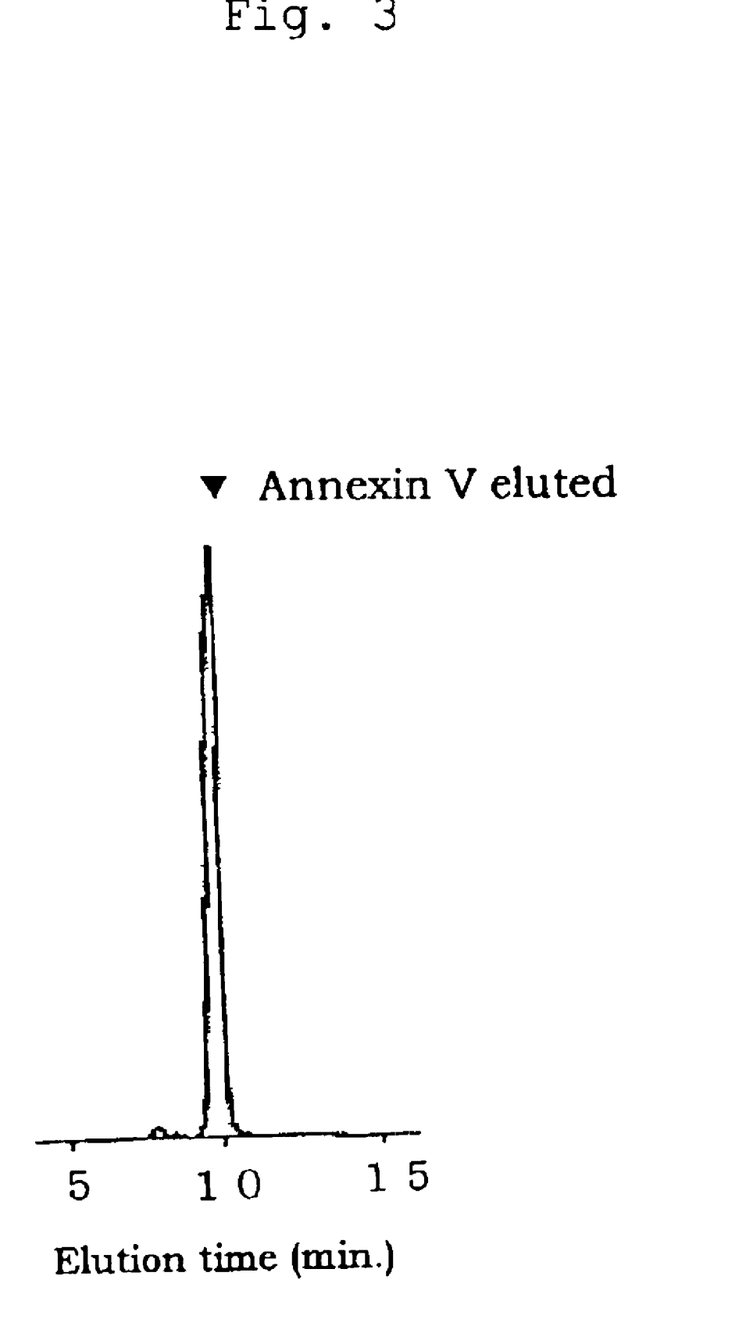
FIG. 3 shows results of gel filtration chromatography for fractions eluted from cation exchange chromatography after washing.

FIG. 3 shows an elution pattern obtained by gel filtration chromatography of fractions eluted from cation exchange chromatography.

Example 3

Purification of Annexin VT from Placenta

One placenta (about 500 g) excepting the amnion and an umbilical cord was sliced into pieces, washed with 2 L physiological saline, and minced with a meat grinder. After adding 400 mL of 50 mM Tris-HCl buffer (pH 7.4) containing 5 mM calcium chloride, 0.1% Triton X-100 and 5 mM benzamidine, the mince was homogenated with a whirling blender. The homogenate was centrifuged at 10,000 rpm for 20 minutes to collect precipitates, which were again suspended in 300 ml of 50 mM Tris-HCl buffer (pH 7.4) containing 50 mM EDTA and homogenated. The homogenate was again centrifuged at 10,000 rpm for 20 minutes and an extract of supernatant was recovered (about 300 mL), to which 63 g ammonium sulfate was added to prepare a 30%-saturated solution of ammonium sulfate. After centrifugation to remove precipitates, to the supernatant was added 54 g ammonium sulfate (60%-saturated ammonium sulfate) and precipitated Annexin VI fraction was recovered. Annexin V could preferentially be recovered in precipitates formed when the salt concentration was raised to 80% saturation of ammonium sulfate.

Figure 4:
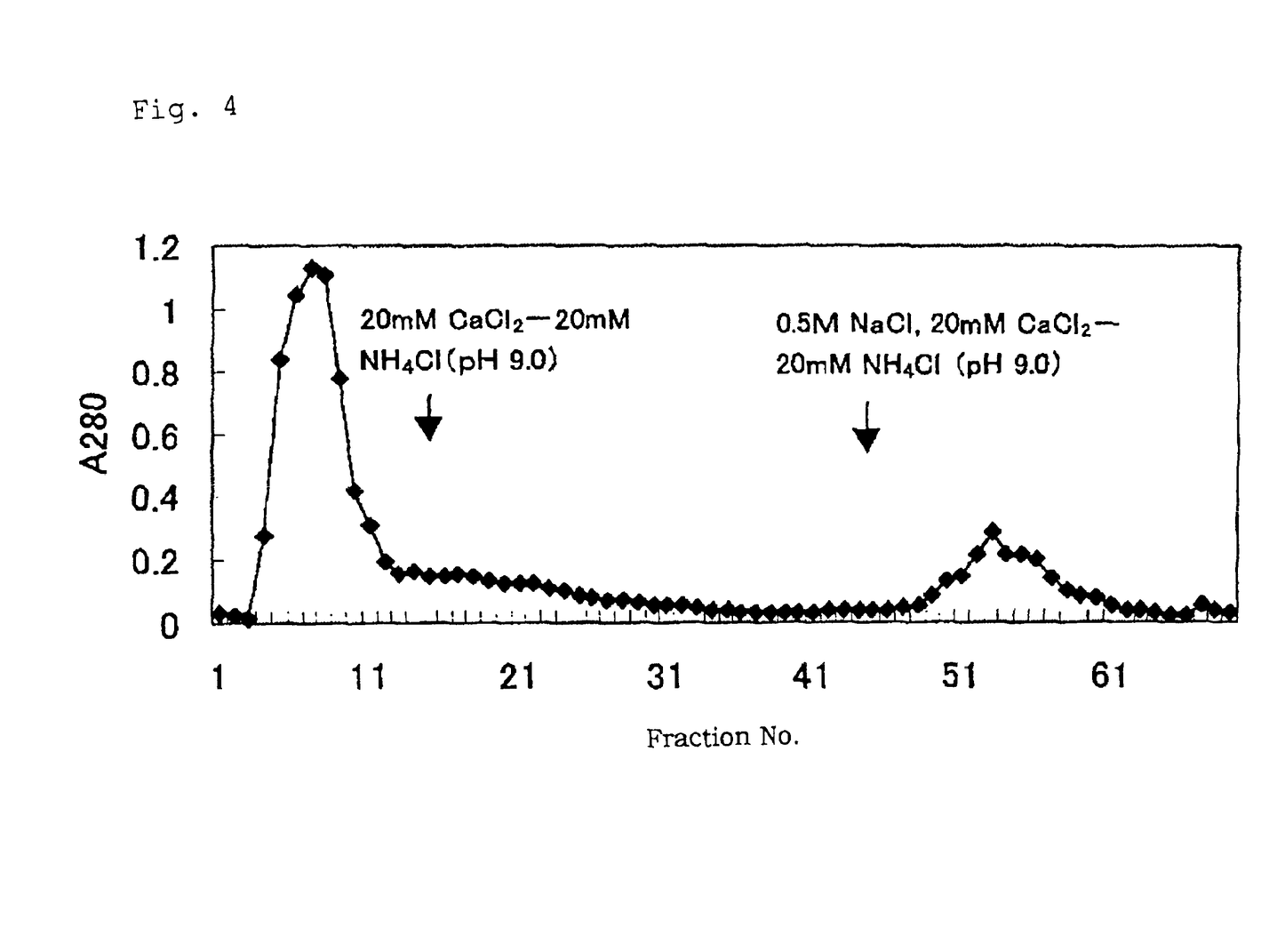
FIG. 4 shows an elution pattern of Annexin VI from SP-Sepharose.
Figure 5:
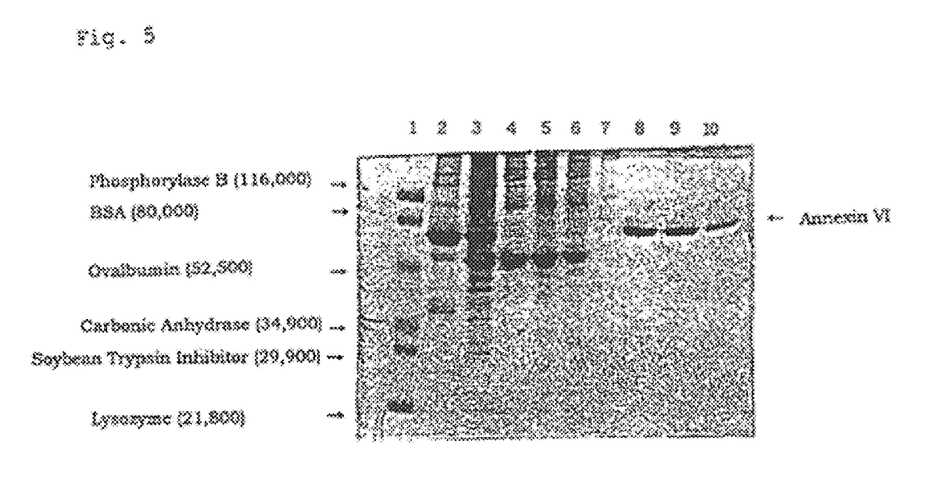
FIG. 5 is a photograph showing results of SDS-PAGE of Annexin VI. Lane 1: BioRad prestained marker proteins; phosphorylase B (116,000), BSA (80,000), ovalbumin (52,500), carbonic anhydrase (34,900), soybean trypsin inhibitor (29,900), lysozyme (21,800); Lane 2: Annexin VI standard; Lane 3: elution with DEAE-Toyopearl (sample); Lane 4: SP-Sepharose, fraction No. 5; Lane 5: fraction No. 7; Lane 6: fraction No. 9; Lane 7: fraction No. 16; Lane 8: fraction No. 51; Lane 9: fraction No. 54; and Lane 10: fraction No. 57.

The precipitates formed with a 60%-saturated solution of ammonium sulfate were dissolved in 50 mM Tris-HCl buffer (pH 7.4) and dialyzed against the same buffer. A dialyzed solution (80 mL) was adsorbed to DEAE-Toyopearl (3×20 cm) equilibrated with the same buffer. After washing with the same buffer, elution was performed by a linear gradient from the same buffer (180 mL) to 50 mM Tris-HCl buffer (pH 7.4) containing 0.3 M NaCl (180 mL)(each fraction: 4 mL/tube). Annexin VI of interest was eluted in fractions No. 46 to No. 50. These Annexin VI fractions were dialyzed against 20 mM ammonium chloride (pH 9.0), to which was added calcium chloride to make finally 20 mM ammonium chloride buffer (pH 9.0) containing 20 mM calcium chloride. The dialyzed solution was adsorbed to SP-Sepharose FF (1.5×8 cm) equilibrated with 20 mM ammonium chloride buffer (pH 9.0) containing 20 mM calcium chloride (FIG. 4; fractions No. 1 to No. 15). After washing with the same buffer, elution was performed with the same buffer supplemented with 0.5 M NaCl (FIG. 4; fractions No. 45 to No. 70). Samples at each stage were analyzed by non-reductive SDS-PAGE and the results are shown in FIG. 5.

Example 4

Purification of Coagulation Factor X

Figure 6:
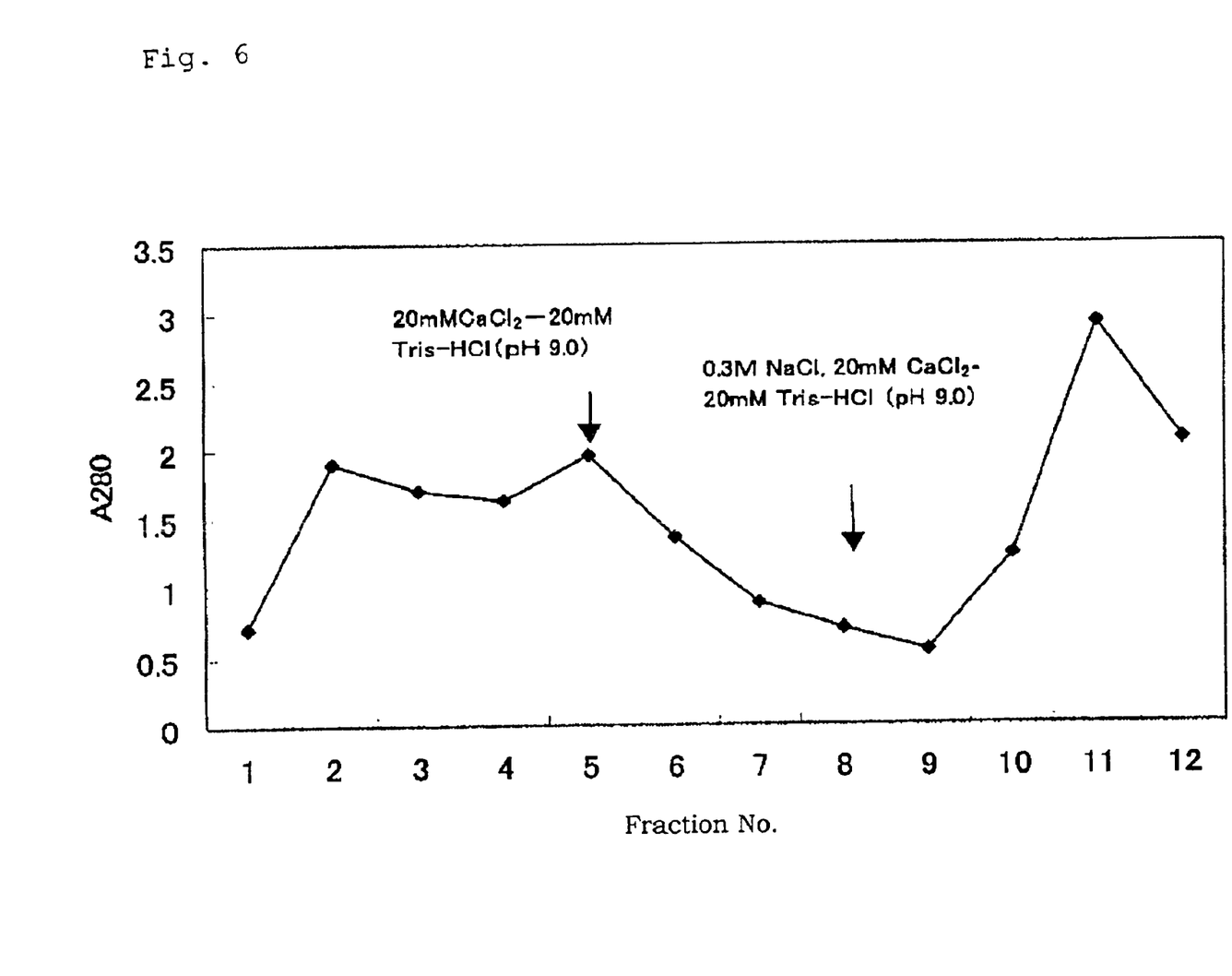
FIG. 6 shows an elution pattern of coagulation factor X from SP-Sepharose.
Figure 7:
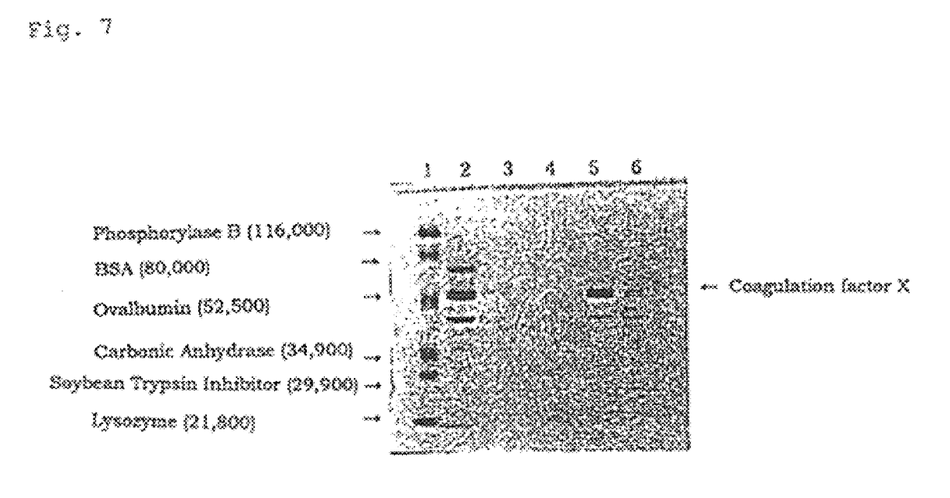
FIG. 7 is a photograph showing results of SDS-PAGE of coagulation factor X. Lane 1: BioRad prestained marker proteins; phosphorylase B (116,000), BSA (80,000), ovalbumin (52,500), carbonic anhydrase (34,900), soybean trypsin inhibitor (29,900), lysozyme (21,800); Lane 2: commercially available coagulation factor X; Lane 3: fraction No. 4; Lane 4: fraction No. 7; Lane 5: fraction No. 11; and Lane 6: fraction No. 12.

Commercially available coagulation factor X (about 1 mg) was dialyzed against 20 mM Tris-HCl buffer (pH 8.0), to which was added one tenth amount of 200 mM calcium chloride to make finally 20 mM Tris-HCl buffer (pH 8.0) containing 20 mM calcium chloride. The dialyzed solution was adsorbed to SP-Sepharose FF (0.8×7 cm) equilibrated with 20 mM Tris-HCl buffer (pH 8.0) containing 20 mM calcium chloride. After washing with 20 mM Tris-HCl buffer (pH 9.0) containing 20 mM calcium chloride, elution was performed with 20 mM Tris-HCl buffer (pH 9.0) containing 0.3 M calcium chloride. In all stages, 5 mM benzamidine was added (Since benzamidine per se exhibits UV absorption at A280, an elution pattern is not explicit; FIG. 6). Fractions at each stage were analyzed by non-reductive SDS-PAGE and the results are shown in FIG. 7.

What is claimed is:

1. A method for purifying a calcium ion-binding protein from a sample containing said protein using a ion-cation exchange carrier, wherein said method comprises
  contacting the sample with the cation exchange carrier in the presence of calcium ions to let the protein be adsorbed to the exchange carrier; and
  eluting the adsorbed calcium ion-binding protein from the exchange carrier by
    (a) decreasing or removing the concentration of said calcium ions
    (b) adding counter ions other than said calcium ions or
    (c) both (a) and (b).

2. The method of claim 1 wherein the adsorption step is performed in the presence of 5 to 100 mM calcium ions.

3. The method of claim 2 wherein the adsorption step is performed in the presence of 10 to 30 mM calcium ions.

4. The method of any one of claims 1 to 3 wherein the adsorption step is performed at a flow rate of 1 to 150 cm/h.

5. The method of claim 4 wherein the adsorption step is performed at a flow rate of 15 to 100 cm/h.

6. The method of claim 4 wherein the adsorption step is performed at a flow rate of 50 to 80 cm/h.

7. The method of claim 1 wherein the elution step is performed by decreasing the concentration of calcium ions to less than 5 mM.

8. The method of claim 1 wherein the elution step is performed by adding 1 to 500 mM of counter ions other than calcium ions.

9. The method of claim 1 wherein the elution step is performed by adding 50 to 500 mM of counter ions other than calcium ions.

10. The method of claim 1 wherein the elution step is performed by adding 50 to 300 mM of counter ions other than calcium ions.

11. The method of claim 1, 8, 9 or 10 wherein said counter ions are selected from the group consisting of $Na^+$, $Li^+$ and $K^+$.

12. The method of claim 1, 7, 8, 9 or 10 wherein the elution step is performed at a flow rate of 1 to 150 cm/h.

13. The method of claim 12 wherein the elution step is performed at a flow rate of 30 to 100 cm/h.

14. The method of claim 12 wherein the elution step is performed at a flow rate of 30 to 80 cm/h.

15. The method of claim 1 wherein the cation exchange carrier is selected from the group consisting of SP-Sepharose, CM-Sepharose, CM-cellulose, SE-cellulose, S-Spherodex and SP-Spherosil.

16. The method of claim 1 wherein the calcium ion-binding protein is selected from the group consisting of Annexins I, II, III, IV, V, VI and VII.

17. The method of claim 1 wherein the sample contains a calcium ion-binding protein prepared by genetic recombination.

18. The method of claim 1 wherein the adsorption and elution steps are performed at pH 5 to 10.

19. The method of claim 18 wherein the adsorption and elution steps are performed at pH 8 to 9.5.

20. The method of claim 19 wherein the adsorption and elution steps are performed at pH 9.

21. The method of claim 1 wherein
  the adsorption step is performed in the presence of 10 to 30 mM calcium ions at pH 8 to 9.5 at a flow rate of 15 to 100 cm/h;
  the elution step is performed at a flow rate of 30 to 80 cm/h by decreasing the concentration of calcium ions to less than 5 mM or by adding 50 to 300 mM counter ions selected from the group consisting of $Na^+$, $Li^+$ and $K^+$;
  the cation exchange carrier is SP-Sepharose;
  the calcium ion-binding protein is Annexin V;
  the sample contains Annexin V prepared by genetic recombination; and
  protease is removed from the sample.

22. The method of claim 1 wherein
  the adsorption step is performed in the presence of 10 to 30 mM calcium ions at pH 8 to 9.5 at a flow rate of 15 to 100 cm/h;
  the elution step is performed at a flow rate of 30 to 80 cm/h by decreasing the concentration of calcium ions to less than 5 mM or by adding 500 mM counter ions selected from the group consisting of $Na^+$, $Li^+$ and $K^+$;
  the cation exchange carrier is SP-Sepharose;
  the calcium ion-binding protein is Annexin VI;
  the sample contains naturally occurring Annexin VI; and
  protease is removed from the sample.

23. A method for purifying a calcium ion-binding protein from a sample containing said protein using a cation exchange carrier, wherein said method comprises contacting the sample with the cation exchange carrier in the presence of calcium ions to let the protein be adsorbed to the carrier.

24. The method of claim 23 wherein said method is performed in the presence of 5 to 100 mM calcium ions.

25. The method of claim 24 wherein said method is performed in the presence of 10 to 30 mM calcium ions.

26. The method of any one of claims 23 to 25 wherein said method is performed at a flow rate of 1 to 150 cm/h.

27. The method of claim 26 wherein said method is performed at a flow rate of 15 to 100 cm/h.

28. The method of claim 26 wherein said method is performed at a flow rate of 50 to 80 cm/h.

29. The method of claim 23 wherein the cation exchange carrier is selected from the group consisting of SP-Sepharose, cM-Sepharose, CM-cellulose, SE-cellulose, S-Spherodex and SP-Spherosil.

30. The method of claim 23 wherein the calcium ion-binding protein is selected from the group consisting of Annexins I, II, III, IV, V, VI and VII.

31. The method of claim 23 wherein the sample contains a calcium ion-binding protein prepared by genetic recombination.

32. The method of claim 23, wherein the method is performed at pH 5 to 10.

33. The method of claim 32 wherein the method is performed at pH 8 to 9.5.

34. The method of claim 33 wherein the method is performed at pH 9.

* * * * *